(12) United States Patent
Vogel et al.

(10) Patent No.: US 11,839,484 B2
(45) Date of Patent: Dec. 12, 2023

(54) METHOD AND DEVICE FOR THE OBJECTIVE DETERMINATION OF CAPILLARY REFILL BEHAVIOR ON A HUMAN BODY SURFACE

(71) Applicant: Fraunhofer-Gesellschaft Zur Foerderung Der Angewandten Forschung E.V., Munich (DE)

(72) Inventors: Uwe Vogel, Dresden (DE); Bernd Richter, Dresden (DE); Torsten Richter, Dresden (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 393 days.

(21) Appl. No.: 17/333,069

(22) Filed: May 28, 2021

(65) Prior Publication Data

US 2021/0369186 A1 Dec. 2, 2021

(30) Foreign Application Priority Data

May 29, 2020 (DE) .................... 10 2020 206 758.9

(51) Int. Cl.
*A61B 5/00* (2006.01)
(52) U.S. Cl.
CPC ............ *A61B 5/442* (2013.01); *A61B 5/0053* (2013.01); *A61B 5/0059* (2013.01); *A61B 5/449* (2013.01);
(Continued)

(58) Field of Classification Search
CPC ..... A61B 5/026; A61B 5/0261; A61B 5/0053; A61B 5/0059; A61B 5/0075; A61B 5/1455
See application file for complete search history.

(56) References Cited

U.S. PATENT DOCUMENTS 6,685,635 B2 * 2/2004 Shani .................. A61B 5/0059
600/476
9,603,559 B2 * 3/2017 Bezzerides .......... A61B 5/6838
(Continued)

FOREIGN PATENT DOCUMENTS

CN         10917658        1/2019
DE      102006030541     12/2007
(Continued)

OTHER PUBLICATIONS

GB Search Report.
(Continued)

*Primary Examiner* — Chu Chuan Liu
(74) *Attorney, Agent, or Firm* — Jacobson Holman PLLC

(57) ABSTRACT

A method for the objective determination of capillary refill behavior on a human body surface in which a spatially and spectrally resolved optical detection is carried out by at least one detector device (1) at a skin surface area (2) having a predefined areal size and outer contour. Subsequently a predefined pressure p constant over the skin surface area (2) is exerted over a predefined time t1; and the pressure effect is ended after expiry of this time t1. The spatially and spectrally resolved optical detection is carried out by the detector device (1) and the respective capillary refill behavior is spatially and temporally determined at a time t2 up to which at least one first threshold value of the measurement values detected simultaneously with spatial resolution has reached the measurement value that had been optically detected before the start of the pressure effect.

13 Claims, 1 Drawing Sheet

(52) U.S. Cl.
CPC ... *A61B 2560/04* (2013.01); *A61B 2562/0233* (2013.01)

(56) References Cited

U.S. PATENT DOCUMENTS

| | | | |
|---|---|---|---|
| 2007/0282182 A1 | 12/2007 | Messerges et al. | |
| 2012/0130211 A1* | 5/2012 | Kobayashi | A61B 5/0059 600/324 |
| 2016/0253800 A1 | 9/2016 | Gurevich et al. | |
| 2017/0209091 A1* | 7/2017 | Weitzel | A61B 5/0059 |

FOREIGN PATENT DOCUMENTS

| | | |
|---|---|---|
| JP | 2016067916 | 5/2016 |
| WO | 2016/0187136 | 11/2016 |
| WO | 2017/009669 | 1/2017 |

OTHER PUBLICATIONS

German Examination Report.
Blaxter et al. An automated quasi-continuous capillary refill timing device. In: Physiological measurement, 2015, vol. 37, No. 1, pp. 83-99.

* cited by examiner

METHOD AND DEVICE FOR THE OBJECTIVE DETERMINATION OF CAPILLARY REFILL BEHAVIOR ON A HUMAN BODY SURFACE

BACKGROUND OF THE INVENTION

The invention relates to a method and a device for the objective determination of capillary refill behavior on a human body surface.

The invention can be used in the field of emergency medicine, intensive care, anesthesiology, outpatient and inpatient hospital care for children and adults. A use is particularly conceivable in the above-named medical fields, but could also be widely used in care facilities for assessing fluid balance.

To date, an examiner has pressed a fingertip onto the fingernail or skin of the patient (for approximately 5 seconds). The time period until the capillary filling has been restored is evaluated. The time until the blanching effect of the examined region caused by pressure has disappeared and the original complexion has again been reached is used as the reference point. This parameter is collected in an orienting manner to evaluate the necessity of a volume substitution and represents a rough parameter for evaluating the microcirculation. The method previously used depends very individually on the respective examiner since the impression depth and the pressure surface used vary.

SUMMARY OF THE INVENTION

It is therefore the object of the invention to make possible a standardized and user-independent examination of the microcirculation within a predefined skin surface area of a patient the initial topographical situation, the quantitative change of the blanching effect situation in relation to the pressure exerted, the inflow dynamics (skin elasticity) and the inflow behavior.

In accordance with the invention, this object is achieved by a method and device according to the claims.

In the method in accordance with the invention, a spatially and spectrally resolved optical detection is carried out by at least one detector device with an optical detector device at a skin surface area having a predefined area size and outer contour. A predefined pressure constant over the skin surface area is subsequently exerted thereon over a predefined time t1. The predefined specific time t1 should here have a value that is between 5 s and 10 s. The constant pressure p should be selected from the pressure interval between 0.4 Mpa and 2 MPa. For reasons of comparison, the predefined time t1, the predefined pressure p, and the predefined size of the area of the skin surface area, as well as its outer contour, should always be the same in all examinations of patients to ensure reproducibility and comparability.

A skin surface area should have an area of at least 100 $mm^2$, preferably at least 150 $mm^2$.

After expiry of this time t1, the pressure effect is ended so that the skin surface area is then subject to the normal pressure of the atmospheric environment.

After the end of the additional pressure effect, the spatially and spectrally resolved optical detection is carried out by the detector device and the respective capillary refill time at the time t2 is determined up to which a pre-settable first threshold value of simultaneously detected measurement values, e.g. at least 90%, preferably at least 95%, of the measurement values detected with spatial resolution, have reached the measurement value that had been optically detected before the start of the pressure effect.

The detected measurement values can be compared with one another in an electronic evaluation unit. The time t2 up to which the preset first threshold value of e.g. at least 90% of the measurement values simultaneously detected with spatial resolution have reached the measurement value that had been detected before the start of the pressure effect can also be determined by the electronic evaluation unit. This is, however, also possible if the measurement values have been detected with temporal resolution by the detector device.

Intensities of electromagnetic radiation are preferably detected by the detector unit at different positions arranged distributed as uniformly as possible within the skin surface area. If individual detectors of the detector device are configured to carry out a spatially resolved measurement, a plurality of intensities of individual selected wavelengths can be determined and taken into account in the evaluation for the determination of capillary refill behavior.

The determination or taking into account of times can be achieved in that the detector device is also configured to carry out a time resolved detection of measurement values. The determination or taking into account of times in the determination of capillary refill behavior can, however, also be achieved by means of an electronic evaluation unit, for example using a timing increment.

The pressure can be exerted mechanically, hydraulically, and/or pneumatically on the skin surface area. For this purpose, the pressure can be applied to the skin surface area by means of a mechanical device at which a stamp is present that temporarily acts on the skin surface area. The stamp can here advantageously be optically transparent so that the detection can take place through it. In this respect, the detector device is arranged at the side of the stamp remote from the skin surface. A stamp should have a front surface that corresponds to the size and outer contour of the area of the skin surface area.

A stamp can, for example, be acted on by means of at least one compression spring having a linear spring characteristic in the direction of the respective skin surface area by a pressure force F1 so that the predefined pressure p acts on the skin surface area.

The pressure p can, however, also be applied pneumatically and hydraulically. A gas and/or a liquid that acts/act on the skin surface area directly or via the detector device in a correspondingly compressed manner in an internally hollow stamp or pressing element can be used for this purpose in a hollow space of a pressing element.

The stamp and/or the detector device can be arranged in the interior of an internally hollow pressing element that can be temporarily brought into contact with the skin surface while surrounding the skin surface area from the outside. It can, however, also be a gas and/or liquid temporarily compressed to the predefined pressure in the interior of the hollow pressing element introducible for the pressure effect on the skin surface. The latter may take place by means of a suitable pressure regulation and/or by means of valves that are connected to a compressed gas line or a compressed gas tank. The gas pressure and/or the liquid pressure can then be maintained in the interior over the time t1. After expiry of the time t1, an outlet valve can, for example, be opened so that the pressure acting at the surface of the skin surface area is reduced down to the environmental pressure of the atmosphere and the spatially and spectrally resolved detection of measurement values is then carried out at least until the reaching of the respective capillary refill behavior.

A combined device that is configured for detection and illumination can be used as the detector device. It can, for example, be an arrangement of bidirectional OLED microdisplays known from DE 10 2006 030 541 B4. A detector device can, however, also be an array arrangement of suitable optical detectors, in particular a hyperspectral imaging camera (HSI camera). It can be advantageous for this purpose to use an additional light source with which at least the skin surface area can be irradiated.

At least 10 measurement values/mm$^2$ should be simultaneously detected and considered by detectors of the detector unit at respective different positions evenly distributed over the respective skin surface area or the area of the skin surface that has the pressure p applied.

Only the wavelengths of the colors of the human skin surface occurring before, during, and after the pressure effect and/or pressure force effect can be considered during the spectrally resolved detection so that the spectral range to be evaluated can be reduced. This can be achieved by suitable optical filtering or by a selection by means of suitable software in the evaluation of the individual measurement values detected with spatial resolution.

In a further development of the invention, an internally hollow pressing element having a predefined dimensioning and geometrical form of the surface coming into direct contact with the skin surface and surrounding the outer margin of the skin surface area completely in the area of the skin surface area can be pressed onto the skin surface during the time of the pressure effect with a predefinable pressure force F2. Before the start of the pressure force effect, a spatially and spectrally resolved optical detection of the image is carried out in the surface area in which the pressing element is brought into contact with the skin surface by the detector device or a further detector device in this surface area. On ending the pressure effect on the skin surface area, the pressing element is removed from or raised from the skin surface and a repeat spatially and spectrally resolved optical detection of measurement values is also carried out in this surface area. The measurement values detected before and during the start of the pressure effect are then continuously compared with the measurement values detected starting from the end of the contact pressure exertion.

A stamp element or pressing element should preferably have a rotationally symmetrical cross-section so that a circular skin surface area is considered. Alternatively, an oval cross-section can also be selected. Polygonal geometries are admittedly possible, but are not to be preferred.

The detector device can be arranged in an internally hollow pressing element. In this process, the outer contour of the detector device should correspond in its shape and dimensioning to the inner contour of the pressing element. In this respect, the detector device can be arranged at a distance from the skin surface area. The detector device can, however, also be pressed against the skin surface area by a stamp or simply pneumatically by compressed gas directly during the time t1 in which a pressure p should be active. It should then be supported with play and optionally longitudinally guided, e.g. supported in longitudinal grooves, to avoid a rotation.

The device can be temporarily fixed in a defined manner to the body part of the person at whom the respective skin surface area is arranged. A tension belt solution or a shape matched fastening option at the corresponding body part can be used for this, for example. In this respect, the respective body part can, for example, be at least partially gripped by means of a clasp to which the device is fastened.

There is advantageously also the possibility of carrying out a two- or three-dimensional spatially resolved detection of the topology of the skin surface area by the detector device before the start of the pressure effect and after the end of the pressure effect and in so doing an evaluation of the temporal return behavior can be carried out by a comparison of the measurement values detected before and after the pressure effect.

Analogously to this, a two- or three-dimensional spatially resolved detection of the topology of the skin surface area can be carried out by the detector device or a further detector device before the start of the pressure force effect exerted by the pressing element and after the end of the pressure force effect and an evaluation of the temporal return behavior can then be carried out by a comparison of the measurement values detected before and after the pressure force effect.

A contact membrane sensitive to a pressure determination can be used for this purpose that can be adhesively fastened to a stamp and with which the area and the time up to the recovery of the contact can be detected after the return of the stamp, preferably to its starting position.

Alternatively, an optical system can be used at an external cylinder, for example at an internally hollow stamp. For this purpose, the optical system can emit suitable electromagnetic radiation into the interior onto the respective skin surface area at a margin facing in the direction of the skin surface. The electromagnetic radiation that is reflected and/or scattered by the surface of the skin surface area can be detected by a detector device suitable for the spatially and spectrally resolved measurement at the oppositely arranged side of the external cylinder or stamp. It is conceivable on an impression of the external cylinder or stamp on the skin surface that a small bulge toward the inside is formed so that it can be detected as a lack of a measurement signal on the opposite side. After compression of the skin and the end of the pressure force exertion, an optical signal can be detected that can then be interrupted again after reaching the starting state or also not (if the skin surface remains partially indented).

On the evaluation of capillary refill behavior, the changes of the spatially and spectrally resolved measurement values occurring after the end of the pressure effect from the outer margin of the skin surface area in the direction of the center of area or in the opposite direction can also be determined.

The measurement values that can be detected by a detector device configured for the spatially and spectrally resolved detection can be processed with suitable evaluation algorithms that can, for example, be stored in an electronic evaluation unit. In this respect, the following criteria can be considered for the determination of the spatially resolved dynamics of the recovery of the starting state in the respective skin surface area:

- a determination of the changes occurring peripherally to centrally or from central to peripheral
- a full-area simultaneous detection and evaluation of detected measurement values over the total skin surface area
- a spot-shaped detection and evaluation, wherein evaluation zones can be structured in individual corresponding sectors and the respective intensity (signal strength) detected with spatial resolution can be analyzed in the course of a specific predefined examination time.

With the start of the pressure effect on the skin surface area, the time can be detected up to which 90% of the individual measurement values simultaneously detected by the detector device have a proportion in the wavelength range between 570 nm and 650 nm below a second threshold value, e.g. less than 5% and thus the blanching time can in turn be determined.

A substantial aspect of the invention consists of the possibility of detecting the capillary refill behavior in a standardized manner and to minimize factors for the parameter determination caused by the respective examiner. Comparative examinations are thus objectivizable, more reliable in their interpretation, and quantifiable. In addition to the main parameter (capillary refill time), the invention is further advantageously configured by allowing the complex determination of the blanching time, capillary refill dynamics, color proportion analysis, pressure depth determination, restoration behavior/elasticity of the examination region.

A certain pressure depth of the skin surface area can be achieved by pressing in the skin and tissue using a standardized pressure applicator such as a stamp having a contact surface on the skin surface or a compressed gas and/or a compressed liquid that acts on the respective skin surface area with the predefined pressure.

A defined pressure p therefore acts on the skin surface over a defined surface in a standardized manner. The consecutive blanching effect can be detected by suitable measurement instruments. The pressure is here maintained over a defined time t1.

The ending of the effect of the pressure exertion on the tissue is detected by the suitable measurement instruments and can be output or evaluated as quantitative parameters.

This allows the presence of a pressure or force sensor configured for the continual determination of the pressure acting on the skin surface area or of the force acting on the skin surface area, by means of which a monitoring within the respective skin surface area is carried out and the measurement values thus detected may be taken into account during evaluation of the capillary refill behavior.

A main parameter is the time-dependent recruitment of blood flow which, in one aspect, corresponds to the capillary refill time and thus approaches the comparability of previous clinical applications. The essential aspect here is the expansion of the possibility for location- and area-specific two-dimensional (i.e. imaging) or three-dimensional detection of the inflow dynamics and decompression behavior continually during the measurement process with regards to restarting skin circulation. This allows not only for a one-dimensional/scalar characterization, but also for additional and time-dependent vectorial evaluation of the inflow dynamics. This allows, as compared to prior art, new evaluation criteria to be derived, e.g. from skin discoloration cluster forms. The optical detector device is preferably configured to determine the skin discoloration as a detector detecting with spatial and spectral resolution and should enable the determination of dynamic changes.

This can e.g. be
a) The determination of the change time that has elapsed up to the reaching of an end state on a pressure exertion or a pressure relief.
b) The determination of the change pattern (e.g.: the change of the complexion from peripheral to central after ending of the pressure effect on the skin surface area).
c) The penetration depth at the exerted standardized pressure and the restoration time of the compressed skin surface area (elasticity) can furthermore be determined and optionally evaluated.

A hollow cylinder or a hollow body having an opening that can be pressed against the skin surface can furthermore be separately usable as a pressing element that or whose opening marginally surrounds the preferably circular skin surface area. The central contact surface can thus be used once with an additional and areally extending hollow cylinder or hollow body on pressure relief. The common pressure effect on the skin surface area used for the evaluation and the contact surface of the pressing element can thus take place from central to peripheral in a common pressure relief or in a staggered pressure relief.

The method in accordance with the invention can, as already mentioned, be carried out e.g. using an arrangement of bidirectional OLED microdisplays known from DE 10 2006 030 541 B4 as a suitable detector. For this purpose in a specific modification, a configuration can be used with an extremely thin transparent encapsulation (barrier and mechanical/chemical/biological protection) between the OLED lighting layer and the layer formed by the detectors (≤50 µm) to achieve an optical imaging 1:1 without additional optical elements.

In detector array, as is the case in particular with a bi-directional microdisplay, using the individual dector elements, it is possible to continually detect which/how many of the individual detector elements are in contact with the skin surface area. This can be achieved both during a time in which a pressure effect is exerted on the respective skin surface area and during a time in which a pressure effect is gradually or suddenly ended.

Alternatively, additional imaging microoptics can also be integrated in a thicker transparent encapsulation of these microdisplays. On a direct bodily contact at the respective surface of a patient to be evaluated (here: the skin surface area) with the encapsulation of the bidirectional OLED microdisplay component, a geometrically precise imaging of the contacting surface can be achieved to the extent of its optical properties (e.g. reflection, absorption) and contrasts and/or colors resulting therefrom.

DESCRIPTION OF THE DRAWINGS

The invention will be explained in more detail by way of example in the following.

There are shown.

Figure 1:
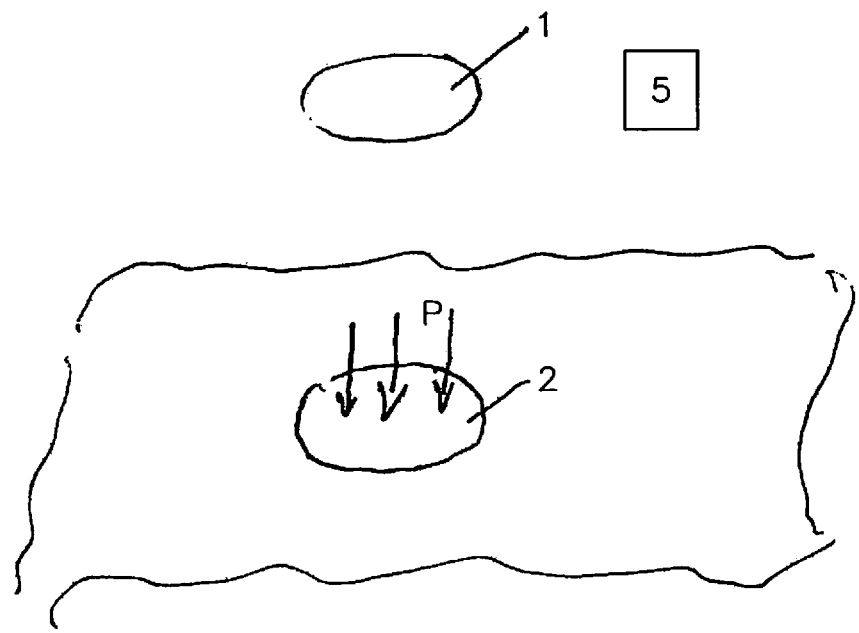
FIG. 1 the principle of the invention in a perspective, roughly schematic representation.

A part of a body surface of a human patient is shown in FIG. 1 in which a circular skin surface area 2 is temporarily pressed in by means of a predefined pressure p during the examination. The skin surface area 2 has a defined specified areal size and geometry and it is imaged on optical detectors of a detector device 1. The detector device here is configured for the spatially and spectrally resolved determination of intensities at different positions within the skin surface area 2.

The measurement values are detected by the individual detectors of the detector device 1 before the pressure p acts on the skin surface area 2 and can be stored in the electronic evaluation unit 5.

The skin surface area 2 is subsequently acted on by the predefined constant pressure p. This is done over the predefined time t1 of 5s.

On expiry of this time t1, the pressure application is ended and the atmospheric environmental pressure then acts on the total skin surface. Bodily fluid displaced from the skin surface area 2 beforehand returns and the blanching effect on the skin surface in the skin surface area 2 caused by the pressure effect is gradually reversed again.

In this respect, measurement values are still detected with spatial and spectral resolution by the detector device 1 and are compared with the starting measurement values. The time up to which at least 90% of the measurement values simultaneously detected with spatial resolution have reached the measurement value that had been optically detected before the start of the pressure effect is determined in this process. This time corresponds to the capillary refill time.

The blanching time can also be determined, as has already been explained in the general part of the description. It is additionally possible to determine the changes of the spatially and spectrally resolved measurement values occurring from the outer margin of the skin surface area 2 in the direction of the center of area after the end of the pressure effect.

Figure 2:
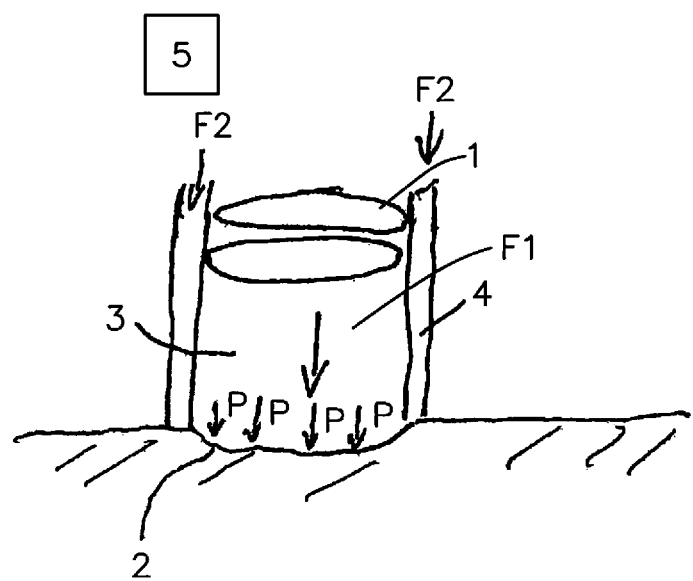
FIG. 2 in a schematic representation, an example of a device in accordance with the invention.

An analog procedure can be followed with the device shown by way of example in FIG. 2.

An internally hollow pressing element 4 is present here that has a circular wall, with the inner diameter of the pressing element 4 corresponding to the outer diameter of the skin surface area 2.

The cylindrical stamp 3 that is pressed against the skin surface in the skin surface area 2 with the constant pressure force F1 is arranged in the pressing element 4 that is pressed against the skin surface with the constant force F2 so that a constant pressure p acts in a settable manner over the time t1 at the skin surface area 2 that should be in the range between 0.2 MPa and 2 MPa.

The detector device 1 is arranged in the interior of the pressing element 4 above the stamp 3. The stamp 3 is guided in the pressing element 4 and is pressed against the surface of the skin surface area 2 with the constant pressure force F1 so that the constant pressure p acts over the time t1 there.

The stamp 3 can be formed from optically transparent polymer such as PMMA.

The determination of capillary refill behavior can otherwise be carried out in an analogous manner to the example in FIG. 1 or as explained in the general part of the description.

Instead of the stamp 3, a compressed gas can there also act temporally in a hollow space of the pressing element 4 above the skin surface area 2 at a constant pressure p over the time t1 and the skin surface can thereby be pressed in and bodily fluid can be displaced there. This does not change anything in the measurement and evaluation in principle. In this case, the pressing element is a hollow body having an opening that is configured to be complementary to the outer contour of the skin surface area 2.

If the pressure effect is achieved by the compressed gas, the gas can act directly on the skin surface. The detector device 1 is then arranged at a spacing from the skin surface.

There is, however, also the possibility of arranging the detector device 1 in the pressing element 4 such that it can be pressed directly against the skin surface in the skin surface area 2 by the compressed gas and such that the pressure effect can thereby be reached by the detector device 1. After the reduction of the inner pressure in the hollow space of the pressing element 4 down to the environmental atmospheric pressure, the detector device 1 lies loosely on the skin surface and the measurement value detection can take place in this position within the skin surface area 2.

The invention claimed is:

1. A method for the objective determination of capillary refill behavior on a human body surface consisting of
    carrying out a spatially and spectrally resolved optical detection by at least one detector device with an optical detector device at a skin surface area having a predefined areal size and outer contour, and subsequently exerting a predefined pressure p constantly over the skin surface area over a predefined time t1; and
    ending the pressure after expiry of this time t1; and carrying out
    the spatially and spectrally resolved optical detection by the at least one detector device and the respective capillary refill behavior is spatially and temporally determined at a time t2 up to which at least one first threshold value of the measurement values detected simultaneously with spatial resolution has reached a measurement value that had been optically detected before a start of a pressure effect.

2. The method in accordance with claim 1, wherein the pressure p is exerted on the skin surface area mechanically or pneumatically or hydraulically.

3. The method in accordance with claim 1, wherein a combined device that is configured for detection and illumination is used as the at least one detector device.

4. The method in accordance with claim 1, including placing an internally hollow pressing element completely surrounding an outer margin of the skin surface area in a region of the skin surface area and having a predefined dimensioning and geometrical design of a surface coming into direct contact with the skin surface area pressed with a predefinable pressure force F2 onto the skin surface area during the time t1 and a spatially and spectrally resolved optical detection of an image is also carried out in this skin surface area by the at least one detector device or by a further detector device before a start of the pressure effect in the skin surface area in which a hollow pressing element is brought into contact with the skin surface area, and on ending of the pressure effect on the skin surface area, the hollow pressing element is removed and a repeat spatially and spectrally resolved optical detection of measurement values is also carried out in the skin surface area, and the measurement values detected before the start of the pressure effect are compared with the measurement values detected after removal of the hollow pressing element.

5. The method in accordance with claim 1, including performing a two- or three-dimensional spatially resolved detection of topology of the skin surface area by the at least one detector device before the start of the pressure effect and up to after the end of the pressure effect; and
    carrying out an evaluation of temporal restoring behavior by a comparison of the measurement values detected before and after the pressure effect.

6. The method in accordance with claim 1, including carrying out a three-dimensional spatially resolved detection of topology of the skin surface area by the at least one detector device or by a further detector device before the start of the pressure effect exerted by a pressing element and up to after the end of the pressure effect; and
    carrying out an evaluation of temporal restoring behavior by a comparison of the measurement values detected before and after the pressure effect in the skin surface area in which the pressing element was in contact with the skin surface area.

7. The method in accordance with claim 1, wherein only wavelengths of colors of human skin surface occurring before, during, and after the pressure effect or a pressure force effect is considered in a spectrally resolved detection.

8. The method in accordance with claim 1, including determining the changes of the spatially and spectrally resolved optical detection measurement values occurring after an end of the pressure effect from an outer margin of the skin surface area in direction of center of area or in opposite direction.

9. The method in accordance with claim 1, with the start of the pressure effect on the skin surface area, detecting time up to which a minimum number of individual measurement values by the at least one detector device have a proportion in wavelength range between 570 nm and 650 nm below a second threshold value and thus blanching time is determined.

10. A device for carrying out the method in accordance with claim 1, wherein a device is present by means of which the predefined pressure p is exerted on the skin surface area over the predefined time t1 and the skin surface area by means of which the at least one detector device configured for the spatially and spectrally resolved optical detection can be monitored is arranged such that a spatially and spectrally resolved optical detection of measurement values can be achieved in the skin surface area before, during, and after the predefined pressure exertion, and the at least one detector device is connected to an electronic evaluation unit or the electronic evaluation unit is integrated in the at least one detector device that is configured to carry out a comparison of the measurement values detected before, during, and after the pressure effect and to determine the time up to which a settable minimum amount of the measurement values detected with spatial resolution have reached a measurement value that had been optically detected before start of the pressure effect.

11. The device in accordance with claim 10, wherein the predefined pressure p can be applied to the skin surface area by means of a mechanical device by which a stamp is present that temporarily acts on the skin surface area or hydraulically or pneumatically, in which a gas or a liquid acts in a correspondingly compressed manner directly via an internally hollow pressing element or via the at least one detector device on the skin surface area.

12. The device in accordance with claim 10, wherein a stamp or the at least one detector device is/are arranged in an interior of an internally hollow pressing element that can be temporarily brought into contact with the skin surface area while surrounding the skin surface area from the outside or
   a gas or liquid temporarily compressed to the predefined pressure p in the interior of a hollow pressing element is introducible for the pressure effect on the skin surface area.

13. The device in accordance with claim 1, wherein a pressure or force sensor configured for the continual determination of pressure acting on the skin surface area or of the force acting on the skin surface area is present.

* * * * *